United States Patent
Shin et al.

(10) Patent No.: US 7,671,039 B2
(45) Date of Patent: Mar. 2, 2010

(54) COMPOSITION CONTAINING BETA-GLUCAN FOR PREVENTION AND TREATMENT OF OSTEOPOROSIS

(75) Inventors: Hyun-Dong Shin, Daegu (KR); Mi-Kyung Son, Daegu (KR); Bok-Ryun Park, Pusan (KR); Chang-Woo Son, Pusan (KR); Hee-Jeong Jang, Pusan (KR)

(73) Assignee: Glucan Corporation, Jinju-Si, Gyeongsangnam-Do (KR)

( * ) Notice: Subject to any disclaimer, the term of this patent is extended or adjusted under 35 U.S.C. 154(b) by 388 days.

(21) Appl. No.: 10/578,133

(22) PCT Filed: Oct. 28, 2004

(86) PCT No.: PCT/KR2004/002746

§ 371 (c)(1),
(2), (4) Date: Jan. 16, 2007

(87) PCT Pub. No.: WO2005/099722

PCT Pub. Date: Oct. 27, 2005

(65) Prior Publication Data

US 2007/0117777 A1    May 24, 2007

(30) Foreign Application Priority Data

Apr. 14, 2004    (KR) .................. 10-2004-0025745

(51) Int. Cl.
*A61K 31/716*    (2006.01)
(52) U.S. Cl. ....................................................... 514/54

(58) Field of Classification Search ............... None
See application file for complete search history.

(56) References Cited

U.S. PATENT DOCUMENTS

2002/0082418 A1*  6/2002  Ikewaki et al. ......... 536/123.12
2004/0058889 A1*  3/2004  Sorgente et al. .............. 514/54

FOREIGN PATENT DOCUMENTS

| JP | 09-56392 | 3/1997 |
| KR | 03-39872 | 5/2003 |
| WO | WO 2004/026239 A2 | 4/2004 |

OTHER PUBLICATIONS

Machine translation of KR 03-39872 (2003).*
Chung, H. et al "Association of interleukin-6 promoter variant with bone mineral density in pre-menopausal women" J. Hum. Genet. (2003) vol. 48, pp. 243-248.*
Klecolt-Glaser, J. et al "Chronic stress and age-related increases in proinflammatory cytokine IL-6" PNAS (2003) vol. 100, No. 15, pp. 9090-9095.*

* cited by examiner

*Primary Examiner*—Leigh C Maier
(74) *Attorney, Agent, or Firm*—Porzio, Bromberg & Newman, P.C.

(57) ABSTRACT

The present invention relates to a composition containing beta-glucan as an effective ingredient for prevention and treatment of osteoporosis. The above captioned beta-glucan is preferably the beta-1.3/1.6 glucan having a lactic acid as a substituent and this beta-1.3/1.6 glucan is preferably produced from *Aureobasidium pullulans* SM2001(KCCM 10307).

1 Claim, 3 Drawing Sheets

[Fig. 1]
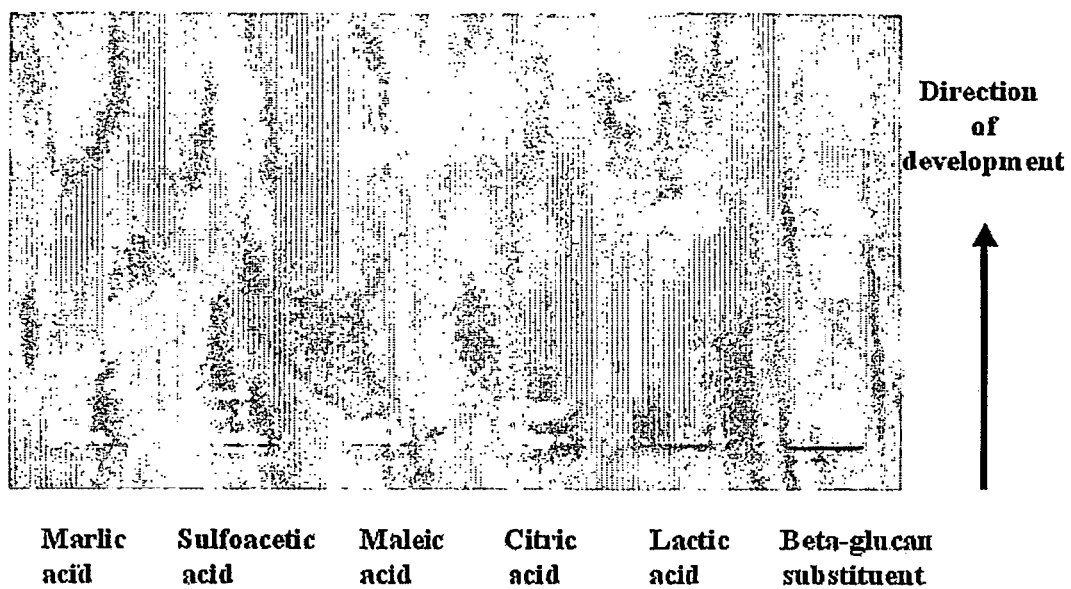
Marlic acid   Sulfoacetic acid   Maleic acid   Citric acid   Lactic acid   Beta-glucan substituent
Direction of development
[Fig. 2]
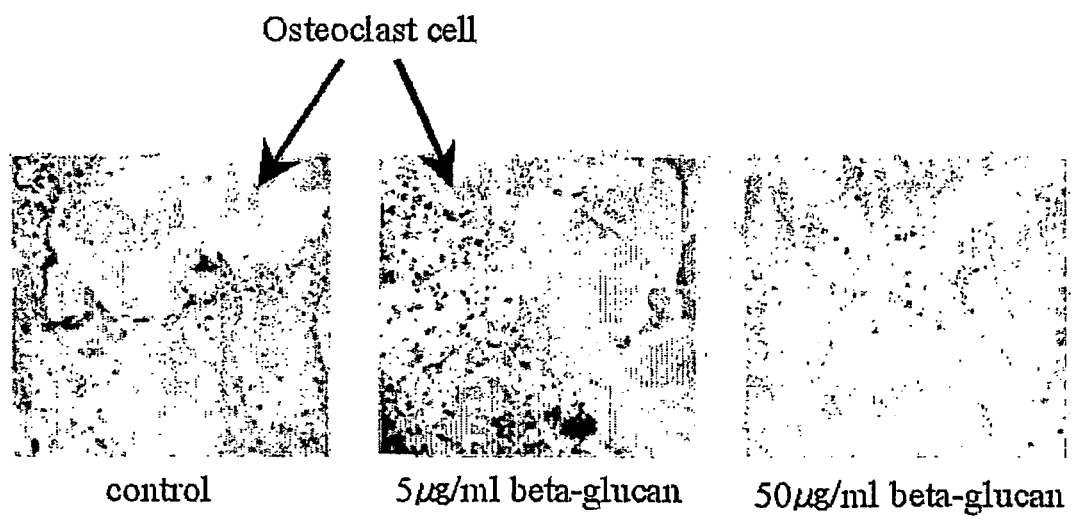
control   5μg/ml beta-glucan   50μg/ml beta-glucan
Osteoclast cell

[Fig. 3]
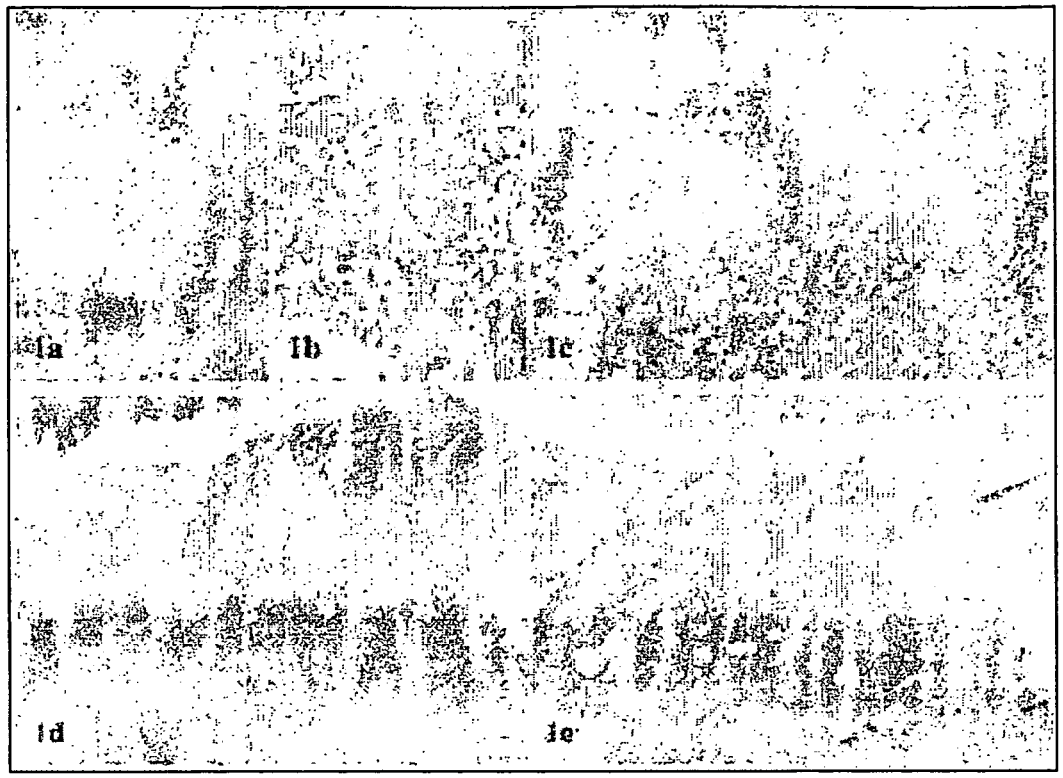
<Remark>
1a: Sham operation; 1b: Control; 1c: Fosamax 10mg/kg;
1d: Beta-glucan 25mg/kg; 1e: Beta-glucan 100mg/kg

[Fig. 4]
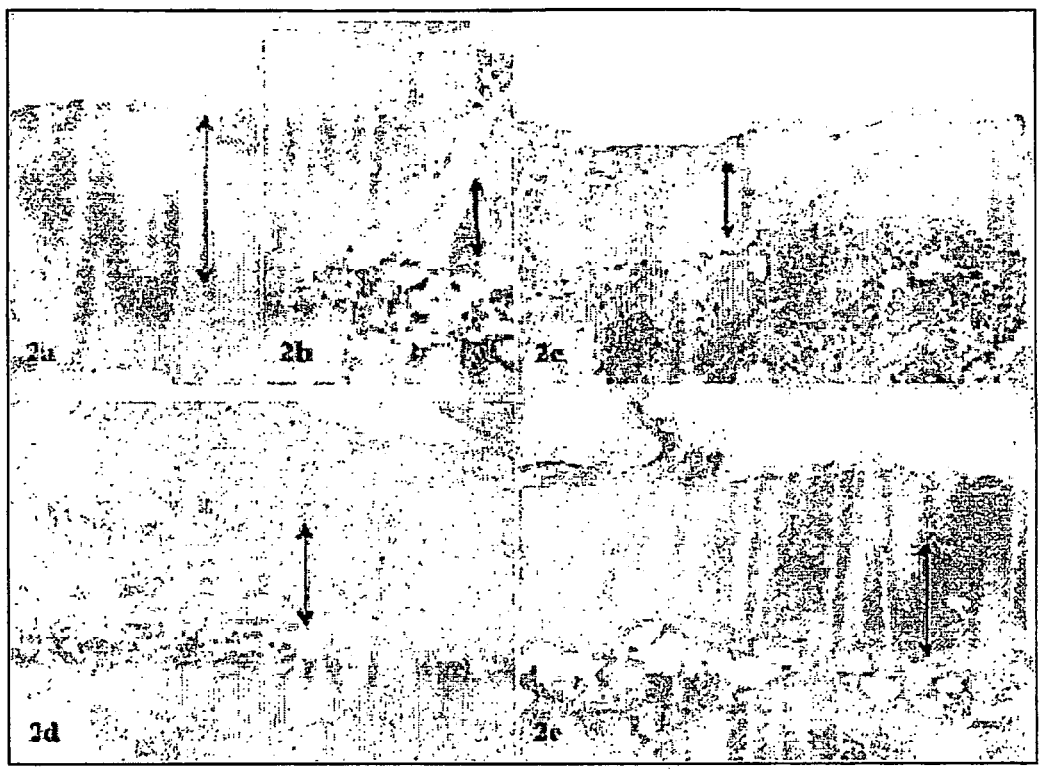
<Remark>
2a: Sham operation; 2b: Control; 2c: Fosamax 10mg/kg;
2d: Beta-glucan 25mg/kg; 2e: Beta-glucan 100mg/kg

COMPOSITION CONTAINING BETA-GLUCAN FOR PREVENTION AND TREATMENT OF OSTEOPOROSIS

TECHNICAL FIELD

The present invention relates to a composition containing beta-glucan for prevention and treatment of osteoporosis. The above captioned beta-glucan is preferably the beta-1,3/1,6 glucan of following Formula 1 having a lactic acid as a substituent and this beta-1,3/1,6 glucan is preferably produced from *Aureobasidium pullulans* SM2001 (KCCM 10307).

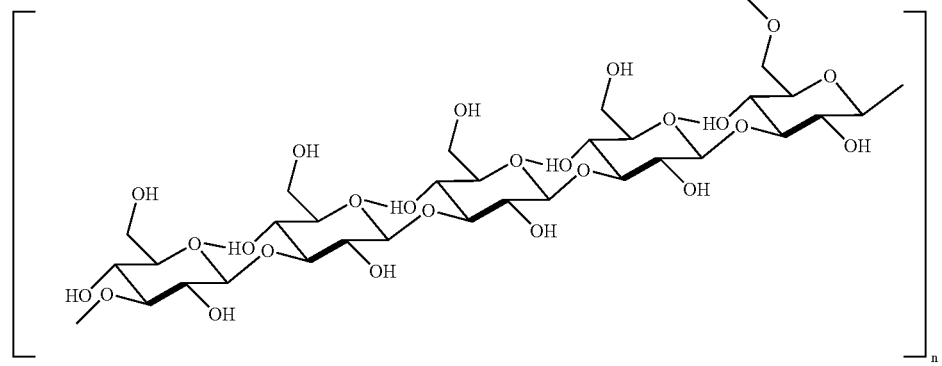

[Formula 1]

BACKGROUND ART

A bone roles a physical supporter of body and also roles a storing place of an inorganic matter, particularly calcium and phosphorus.

A bone is consisted of an inorganic matter whose principle ingredient is phosphorus and calcium, an organic matter whose principle ingredient is type I collagen, and water. Amount of bone increase continuously, and then reach to the highest point about age of 20 years, and continuously decrease from after about age of 30 years. Particularly the Yeoman is faced abrupt lose of bone during 5-10 years after postmenopausal at about age of 50 years due to deficient of estrogen. The strength of bone is originated in a density of bone, and it gives an effect to microstructure, size and geometry of bone. A bone is an organ that has an outer layer consisted with a connective tissue deposited a mineral and an inside having a bone marrow being in a bone marrow cavity. Also, a bone marrow has hematopoiesis, and a heniatopoietic stem cell of bone marrow is differentiated to an osteoclast cell absorbing a bone and stromal cell of bone marrow is differentiated to an osteoblast cell building up a bone (Manolagas S C, Jilka R L: Bone marrow, cytokines, and bone remodeling. *N. Engl. J. Med.* 332 (5):305-11, 1995).

An osteoporosis is a basic disease of skeletal system related to a bone such as myeloma, bone arthritis, hypercalcemia and so fortrh, and increases sensitivity for fracture and decrease strength of bone. At bone, a formation of bone by osteoblast cell and a destruction of bone by osteoclast cell is always coincided, and reconstruction process is consistently happened to normal function of bone. However, if a balance of reconstruction process between absorbance of bone and formation of bone incline to absorbance of bone, absorbance of bone by osteoclast cell is increased, and decrease of bone amount and weakening of bone strength is happened to be induced osteoporosis being increased danger of fracture in conclusion. The pharmaceutical preparation for treating osteoporosis being used currently may be classified an inhibiting agent of bone absorbance and an accelerating agent of bone formation.

An inhibiting agent of bone absorbance is female honnone, bisphosphonate, selective follicle hormone receptor substance, calcitonine, and so on, an accelerating of bone formation is a pharmaceutical preparation for parathyroid gland hormone, active vitamin D and the like. However, the absorbent ratio of bisphosphonate as a strong inhibiting agent of bone absorbance is low and it has side effect for gastroenteric gland, an agent for follicle hormone also has a possibility being capable of inducing a breast cancer and uterine cancer when dosing for long time. Therefore, there has being a research to improve a drawback of a pharmaceutical preparation being used currently (David Goltzrnan. Discoveries, Drugs and Skeletal Disorders, *nature review* 1, 784-796 (October 2002)).

For an action of bone remodeling, while OPG (osteoprotegerin), RANTKL (receptor activator of nuclear factor κB ligand), RANK (receptor activator of nuclear factor κB) protein which is essential for activating and divergence of bone sub-cell and osteoclast cell and substance is identified at about 2000 year, and its role is found, hormones such as follicle hormone and parathyroid gland hormone, cytokines such as inteleukin-1 (IL-1) and tumor necrosis factor-α (TNF-α), and growth factor such as inmmune growth factor (IGF) which effect to bone metabolism is examined and a research for these protein is being progressed. Except for the above, a research is being progressed for protein effecting to adhesion and activation for bone of osteoclast cell, acting progress for transferring signal, and translating factor (AP1, c-src), and various growth factor (TGF-β, PDGF, FGF), lipid regulating factors (for example, PPAR γ) and the like (J H Tobias, A M Flanagan, A M Scutt: Novel therapeutic targets in osteoporosis. *Expert Opin. Ther. Targets* 6(1):41-56, 2002).

On the other hand, it is only an agent for parathyroid gland hormone that approved from FDA, USA as a pharmaceutical preparation for treating osteoporosis, an accelerating agent of bone formation but not an inhibiting agent of bone absorbance. Most inhibiting agent of bone absorbance applied to treat osteoporosis show its function by reducing a bone turnover rate, therefore in case that a lose of bone had already been high progressed or in case of the patient having a high bone turnover rate or when considering prevention of fracture with long term, the necessity for an accelerating agent of bone formation is gradually increased. Therefore, a research is being progressed for targeting a osteoblast cell undertaking a formation of bone other than conventional fluorine compound and parathyroid gland hormone (S. K, Yeem, Bone Formation-Stimulating Agent As Agent Treating Osteoporosis, *Korean Endocrine Association*, Vol. 14-2, 1999).

It is recently found that autoimmune arthritis and osteoporosis is closely related to unbalance of various cytokines playing an important role for immunoactivity control of human body. For example, OPG, RANK, RANKL controlling a divergence and activation of osteoclast cell is essential factor for controlling a divergence and production of immunocell, and RNAKL induce production of osteoclast cell and destruction of bone by activated T cell. Such as the above description, it is proved that a metabolism of immuno-system and bone functionally related to each other, it is focused to development of pharmaceutical preparation for treating and preventing osteoporosis through normalization of immuno-controlling function. (Y. A, Kong; Osteoprotegerin ligand: Controlling factor for immune reaction and bone, *Biowave* vol. 4 No. 5, 2002). Particularly, it is also necessary demanded for development of novel material being capable of replacing a conventional hormone agent and organic compound obtained by chemical synthesis having toxicity and side effect such as estrogen. Therefore, since these novel materials can be found from a natural object, it is actively progressed a trial to invent a new drug from a natural object.

The present inventors recognize the above conventional problem, and search a natural object that remarkably reduce an activity of osteoclast cell and concurrently activate osteoblast cell facilitating production of bone. As the result, the present inventors notice possibility that utilize beta-glucan known as having immunity increase and anticancer effect for treating osteoporosis.

DESCRIPTION OF DRAWINGS

Other objects and aspects of the present invention will become apparent from the following description of embodiments with reference to the accompanying drawing in which:

FIG. 1 is a thin layer liquid chromatography showing kind of organic acid being substituted at water soluble beta-1,3/1,6-glucan derived from *Aureobasidium pullulans* SM2001.

FIG. 2 is photograph showing an inhibiting effect of osteoclast cell formation by water soluble beta-1,3/1,6-glucan derived from *Aureobasidium pullulans* SM2001.

FIG. 3 is photograph showing histomorphometric changes of cutting part at the left thigh after administrating beta-glucan to experimental animal.

FIG. 4 is photograph showing cortical bone of the left thigh after administrating beta-glucan to experimental animal.

DISCLOSURE OF INVENTION

Technical Problem

The present invention is to search a new bioactive material showing a function inhibiting bone absorbance or facilitating bone production, and provide a pharmaceutical composition for treating and preventing osteoporosis comprising it as active ingredient.

Technical Solution

The above-mentioned object of the present invention can be achieved by preparing water soluble beta-1,3/1,6-glucan (acidic β1,3/1,6-glucan) from upper layer of broth of *Aureobasidium pullulans* SM2001 (KCCM 10307), investigating its structural character and an effect of said material on formation of osteoclast cell and activation of osteoblast cell, investigating an effect of beta-glucan derived from pustulan, Youngi mushroom and Chima mushroom other than said beta-glucan on formation of osteoclast cell and activation of osteoblast cell, and confirming an effect of beta-glucan for treating and preventing osteoporosis.

The present invention relates to a composition containing beta-glucan for prevention and treatment of osteoporosis. The above captioned beta-glucan is preferably the beta-1,3/1,6 glucan of following Formula 1 having a lactic acid as a substituent and this beta-1,3/1,6 glucan is preferably produced from *Aureobasidium pullulans* SM2001 (KCCM 10307)

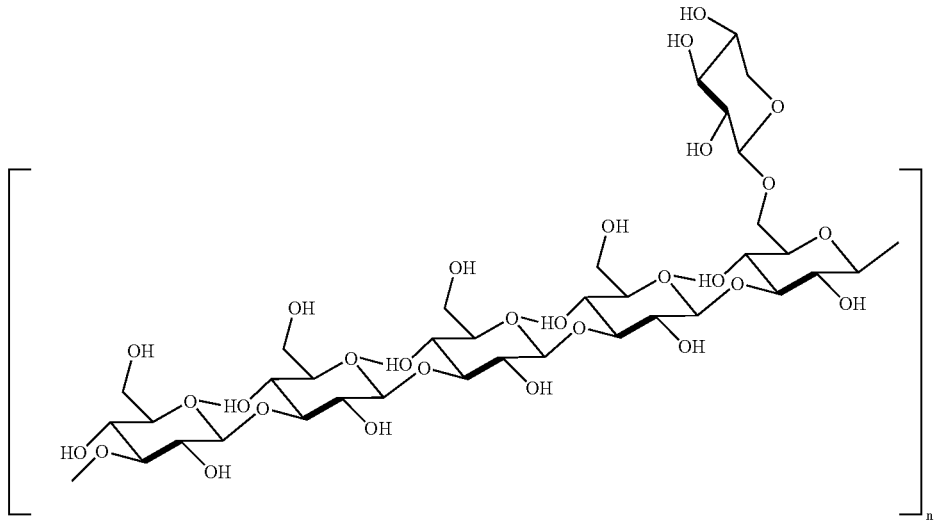

[Formula 1]

The beta-glucan according to the present invention has an effect inhibiting activity of osteoclast cell, therefore it may be effectively used for prevention and treatment of osteoporosis. Particularly, the beta-1,3/1,6-glucan produced by *Aureobasidium pullulans* SM2001 (KCCM 10307) strain is substituted with lactic acid group and is acidic polysaccharides of water soluble which is easily soluble in water, thereby having a bioactivity which remarkably inhibit an activity of osteoclast cell reducing a density of bone by absorbing calcium resident in bone and concurrently highly activate osteoblast cell accelerating a formation of bone, and can be used for prevention and treatment of osteoporosis.

According to the present invention, the water soluble beta-1,3/1,6-glucan can be produced by inoculating strain, *Aureobasidium pullulans* SM2001 (KCCM 10307) described in Korean Patent Application 2001-0071242 filed by the present applicant, at a medium containing carbon source, nitrogen source and inorganic salts with 3 to 5% (v/v) and culturing it under aerobic condition for 3 days at 25° C. with 200 rpm, and then removing microbial cell by centrifuging the cultured broth, and precipitating the produced beta-1,3/1,6-glucan by adding ethanol with 2 times and mixing, and recovering it, and purifying by lyophilization.

It had been proved that the beta-1,3/1,6-glucan obtained by the above method is the water soluble beta-1,3/1,6-glucan of acidic form, and it had been confinrned that lactic acid present in this glucan as substituted group by analyzing its branching degree and polysaccharide chain with a thin layer liquid chromatography and a high performance liquid chromatography after treating it with β-1,3-glucanase and sodium hydroxide.

We research an effect on osteoclast cell formation derived from mice and an activation of osteoblast cell accelerating production of bone of the beta-1,3/1,6-glucan obtained by the above method. As the result, the water soluble beta-1,3/1,6-glucan derived from *Aureobasidium pullulans* shows that remarkably inhibit an activity of osteoclast cell absorbing bone and concurrently highly activate osteoblast cell accelerating a formation of bone. With the above result, the water soluble beta-1,3/1,6-glucan derived from *Aureobasidium pullulans* SM2001 can be provided as usage for prevention and treatment of osteoporosis.

Also, we searched an effect on osteoclast cell formation and an activity of osteoblast cell of beta-glucan derived from yeast, beta-glucan derived from pustulan, Youngi mushroom and Chima mushroom other than said beta-glucan derived from *Aureobasidium pullulans* SM2001. As the result, we confirm that all beta-glucan can inhibit osteoclast cell formation. With the above result, beta-glucan can be provided as usage for prevention and treatment of osteoporosis.

According to the present invention, the composition for preventing and treating osteoporosis contains beta-glucan, preferably beta-glucan of formula 1, more preferably beta-glucan produced from *Aureobasidium pullulans* SM2001 with 5~900 mg/kg, preferably 20~200 mg/kg.

A greater understanding of the present invention and its concomitant advantages will be obtained by referring to the following Example provided, but it is not limit the scope of the present invention.

Advantageous Effects

The above-described present invention provides a fact that beta-glucan has an effect inhibiting osteoclast cell activity, therefore it can be effectively used for prevention and treatment of osteoporosis, particularly the beta-1,3/1,6-glucan produced by *Aureobasidium pullulans* SM2001 (KCCM 10307) strain is being substituted with lactic acid group, and is acidic polysaccharides of water soluble which is easily soluble in water, thereby having a bioactivity which remarkably inhibit an activity of osteoclast cell reducing a density of bone by absorbing calcium resident in bone and concurrently highly activate osteoblast cell accelerating a formation of bone, and can be used for prevention and treatment of osteoporosis. The water soluble beta-1,3/1,6-glucan of acidic form can be also produced economically through a mass cultivation of *Aureobasidium pullulans* SM2001, and it is a natural objection having a stability to human body, and can be also expected to have an effect added such as an immunity increase for human body, therefore the present invention is very useful for a health and a pharmaceutical industry.

BEST MODE

Example 1

Preparing the Water Soluble Beta-1,3/1,6-glucan Derived from *Aureobasidium pullulans* SM2001

To produce the water soluble beta-1,3/1,6-glucan for prevention and treatment of osteoporosis, *Aureobasidium pullulans* SM2001 is cultured in the culturing medium containing 5 g/L of $K_2HPO_4$, 1 g/L of NaCl, 0.2 g/L, of $MgSO_4.7H_2O$, 0.6 g/L of $(NH_4)_2SO_4$ and 2.5 g/L of yeast extraction. At culturing, as carbon source, glucose is used after sterilization, and it is mixed to a sterilized medium with 2% (v/v) at a germ-free condition. A pre-cultivation is carried out with a procedure that *Aureobasidium pullulans* SM2001 cultured during predetermined times is taken with platinum needle to inoculate to 250 ml of a sterilized flask containing 50 ml of medium, and then is shake-cultured with 180 rpm at 30° C. during 72 hours. A main-cultivation is carried out with a procedure that a culture fluid cultured by pre-cultivation is taken to inoculate to 500 ml of a sterilized flask containing 150 ml of same medium with 5% (v/v), and then is cultured by the same method with pre-cultivation during 3 days.

The above culture fluid is centrifuged with 8000×g during 20 minutes to remove a microbial cell and recover upper layer. To said upper layer, 95% ethanol of 2 times volume is added, and mixed well, and then stand over night at 4° C. The above liquid is centrifuged with 8000×g during 20 minutes to remove upper layer. And than a precipitate is washed with 95% ethanol two times. The washed precipitate is dissolved in a proper amount of distilled water, and then dialyzed during 2 days with exchanging a distilled water 5 times to remove a material having low molecular weight including salt component. A dialysis membrane having an exclusion molecular weight of 13,000 dalton is used, a fraction inside said dialysis is dried with freezing at vacuum state and recovered to obtain a powder of water soluble beta-1,3/1,6-glucan of 3 g per 1 liter of culture fluid.

Example 2

Analysis of a Branch Degree and a Substituted Organic Acid of Water Soluble Beta-1,3/1,6-glucan Derived from *Aureobasidium pullulans* SM2001

To analyze a branch degree of water soluble beta-1,3/1,6-glucan derived from *Aureobasidium pullulans* SM2001 prepared by example 1, to acetic acid buffer (pH 4.0) dissolved beta-1,3/1,6-glucan with concentration of 1.0% (w/v), 50 mg of endo-β1,3-glucanase (from *Rhizoctonia solani*, Sigma Co.) is added and dissolved, and then analyzed a produced amount of glucose, a product of reaction, and gentibiose coupled glucose with beta-1,6-glucoside bond, while allowing reaction at 40° C. during 2 hours.

The result is shown at table 1. From this result, we can notice that the water soluble beta-1,3/1,6-glucan derived from *Aureobasidium pullulans* SM2001 reach an equilibrium state with hydrolysis rate of 42.5% after 1 hour from reaction, and the molar ratio for a produced gentibiose and glucose at this time is average 4:1, and it is branched beta-glucan that coupled one molecular of gentibiose being beta-1,6 bond per 5 molecular of glucose being bound beta-1,3 bond.

TABLE 1

Produced molar ratio for gentibiose and glucose produced in hydrolysis of beta-1,3/1,6-glucan using endo beta-1,3-glucanase.

| Reaction time (min.) | Hydrolysis rate (%) | Glucose/gentibiose(molar ratio) |
|---|---|---|
| 10 | 15.8 | 2.58 |
| 30 | 19.5 | 3.55 |
| 60 | 42.5 | 4.05 |
| 90 | 42.8 | 5.86 |

To investigate the kind of organic acid substituted at the water soluble beta-1,3/1,6-glucan derived from *Aureobasidium pullulanss* SM001, beta-1,3/1,6-glucan prepared from example 1 is dissolved at 1.0M sodium hydroxide solution and stirred at 70° C. during 2 hours to separate a substituted organic acid. After completion of reaction, ethanol of two times volume is added to the reactant to precipitate beta-glucan, and then absorbed to a strong anionic ion-exchange resin, Dowex 50W-X8 to remove sodium hydroxide. And organic acid component is eluted with 4N formic acid after non-absorbance eluting solution including organic acid is absorbed to cationic ion-exchange resin, DEAE-Sephadex. The eluted organic acid component is dried with vacuum, and dissolved with distilled water, and then separated and developed organic acid component with a thin layer liquid chromatography using 1-butanol/pyridine/water (6/4/3) mixture solution as developing solvent, and finely confirmed a kind of organic acid by staining it with staining reagent, 0.5% (w/v) bromophenol blue ethanol solution.

The result is shown at FIG. 1. From this result, we can confirm that the kind of organic acid substituted at the water soluble beta-1,3/1,6-glucan derived from *Aureobasidiumn pullulans* SM2001 is lactic acid. With the above result, the water soluble beta-1,3/1,6-glucan derived from *Aureobasidium pullulans* SM2001 according to the present invention is water soluble, and acidic beta-1,3/1,6- glucan having branched structure as FIG. 2.

Example 3

Effect Inhibiting Osteoclast Cell Formation of the Water Soluble Beta-1,3/1,6-glucan Derived From *Aureobasidium Pullulans* SM2001

1) Separation of Osteoblast Cell From Mice

ICR mouse of age of 1 day is dipped in ethanol and then incised skull using a scissors and a pincette. The collected muscle of skull and debride are removed from sterilized α-minimum essential medium (α-MEM), and then 10 ml of 0.2% collagen decomposition enzyme (Gibco BRL) is added. And it is treated with 200 rpm during 20 minutes at 37° C. and discard osteoblast cell obtained at the first, and take a reactant upper layer with same method up to 2 to 5 times. To the collected upper layer, PBS (phosphate buffered saline) buffer is added, and then centrifuged with 1,200 rpm during 5 minutes. The collected osteoblast cell is cultured for 2-3 days after being added it at α-MEM medium containing 10% FBS (fetal bovine serum), and then it is recovered and applied to activity experiment of osteoblast cell or osteoclast cell formation inhibition experiment after freezing storage.

2) Preparing a Bone Marrow Cell

The cervical vertebral of ddy mouse of age of 6 weeks is dislocated its bone, and extract germ-freely the tibia and the femur and remove a contaminant. A bone marrow cell is obtained by inserting α-MEM in the above bone using a injector. The obtained bone marrow cell is disaggregated by using the above injector, and then centrifuged with 1,200 rpm during 5 minutes. After removing the upper layer, 5 ml of tris-hydrochloric acid buffer (0.8% ammonium chloride, pH 7.5) is added to destruct erythrocyte, and mixed well, and centrifuged with the same condition to give only a bone marrow cell.

3) Preparing a Sample

The water soluble beta-1,3/1,6-glucan derived from *Aureobasidium pullulans* SM2001 prepared from the above example 1 is dissolved in distilled water or DMSO (dimethylsulfoxide) with concentration of $2.5 \times 10^{-3}$ g/ml, and then filtrated with 0.25 μm of filter. This filtrate is used at an experiment after being diluted to concentration of $2 \times 10^{-6}$ g/ml, $2 \times 10^{-8}$, and $2 \times 10^{-7}$ with α-MEM differentiating medium containing 10% FBS solution. The differentiating medium is prepared by adding an active element, 1,25-dihydroxy-vitamin $D_3$ (10 ng/ml) and dexamethasone (0.1 μM), to α-MEM.

4) Co-cultivation and Osteoclast Cell Formation Inhibition Experiment

The osteoblast cell prepared by the above 1) is diluted to $5 \times 10^{-3}/50$ μl α-MEM, and then distribute 96 well plate. The bone marrow cell prepared by the above 2) is diluted to concentration of $5 \times 10^{-5}/50$ μl α-MEM, and added to the above 96 well plate. Next, the water soluble beta-1,3/1,6-glucan derived from *Aureobasidium pullulans* SM2001 prepared by the above 3) and differentiating factor solution are added each 100 μl, and then discarded 100 μl of medium and solution and newly added 100 μl each 2 days. After 6 days of cultivation, the culture fluid is removed and washed with PBS provided that a matured osteoclast cell is appeared on the microscope. And 10% formalin is added to fix, and then washed with PBS again, and dried. To counter a number of matured osteoclast cell, a staining liquid for labeling enzyme TRAP (Tartrate-resistant acid phosphatase, hereinafter, refer to "TRAP") of osteoclast cell is added with 100 μl, and reacted during 10 minutes. After confirming dyeing, we discard the staining liquid and wash with PBS, and then counter a number of matured osteoclast cell having nucleus over 10 stained with TRAP.

5) Analysis of Result

A degree for osteoclast cell formation inhibition is expressed with percentage of inhibition by comparing matured osteoclast cell measured at the above 4) with the control group, which is carried out with above n=5 each 20 concentration of sample, and repeated above 3 times. The result is shown at FIG. 3 and table 2.

TABLE 2

Effect on osteoclast cell formation inhibition of water soluble beta-1,3/1,6-glucan derived from *Aureobasidium pullulans* SM2001

| beta-glucan conc. (μg/ml) | Number of osteoclast cell (No.) | osteoclast cell formation inhibition percentage (%) |
| --- | --- | --- |
| 50 | 0 ± 0 | 100 ± 0 |
| 25 | 0.4 ± 0.9 | 99.6 ± 1.0 |
| 5 | 20.7 ± 5.7 | 79.2 ± 6.2 |
| 0.5 | 77.3 ± 6.7 | 14.2 ± 7.3 |
| control | 91.3 ± 9.7 | |

Remark)
IC50: 0.92 μg/ml

As shown the FIG. 3 and table 2, the water soluble beta-1,3/1,6-glucan of acidic form derived from *Aureobasidium pullulans* SM2001 inhibit to differentiate to osteoclast cell perfectly at concentration of 50 μg/ml while the control group form Osteoclast cell of 91.3±9.7. From this result, it can be determined that the compound according to the present invention is effective for prevention and treatment of osteoporosis since it inhibit an absorbance of bone by inhibiting a formation of osteoclast cell.

Example 4

Effect Inhibiting Osteoclast Cell Formation Depending on a kind of Beta-glucan

As shown the above example 3, the beta-glucan derived from *Aureobasidium pullulans* SM2001 show an excellent effect inhibiting osteoclast cell formation. Therefore, we try to research an effect inhibiting osteoclast cell formation depending on a kind of beta-glucan. A sample of beta-glucan derived from yeast, pustulan, Youngi mushroom and Chima mushroom other than said beta-glucan derived from SM2001 strain are each prepared according to the same method of the above example 3. An effect of these samples on inhibiting osteoclast cell formation is searched and its result is shown at table 3.

As shown the above table 3, most beta-glucan show an effect inhibiting osteoclast cell formation, particularly the water soluble beta-1,3/1,6-glucan of acidic form derived from *Aureobasidium pullulans* SM2001 show most excellent effect inhibiting osteoclast cell formation.

Example 5

Effect Accelerating Osteoblast Cell Formation of the Water Soluble Beta-1,3/1,6-glucan Derived from *Aureobasidium pullullans* SM2001

It is necessary to search a possibility as an accelerating agent of bone formation other than an absorbing agent of bone to find out a value as preventing and treating agent of osteoporosis. Therefore, we search an effect accelerating osteoblast cell formation of the water soluble beta-1,3/1,6-glucan derived from *Aureobasidium pullullans* SM2001.

1) Preparing Osteoblast Cell

An osteoblast cell of mouse is prepared by the same method with the above example 1-1). The prepared osteoblast cell is divided and inoculated to 12 well plates including 2 ml of α-MEM containing 10% FBS to concentration of $5 \times 10^{-5}$ cell/well. And then it is cultured at 37° C. during 24 hours, and after completion of cultivation, the medium is removed perfectly and the drug is added.

2) Preparing Sample and Dyeing Liquid

A differentiating medium for osteoblast cell is prepared by adding osteoblast cell differentiation and an active factor, ascorbic acid (0.1 mg/ml) and β-glycerolphosphate (5 mM), to α-MEM containing 10% FBS, and then mixing it. With using the above differentiating medium, a sample of beta-1,3/1,6-glucan concentrated to $2.5 \times 10^{-3}$ g/ml is diluted to concentration of $1 \times 10^{-5}$ and $1 \times 10^{-7}$ g/ml.

To prepare AR-S dyeing liquid (40 mM Alizarin), 136.8mg of Alizarin Red S produced by Sigma Co. is dissolved in 10 mil of water and then filtrated with 0.25 μm filter. To Vonkossa (5% silver nitrate) dyeing, 5 g of silver nitrate is dissolved in a ultra-pure water to 100 ml of final volume to make a dyeing liquid of 5% (w/v) of silver nitrate. A cetylpyrinidinium chloride solution required for elution experiment of AR-S is prepared by dissolving cetylpyrinidinium chloride in 10 mM sodium phosphate buffer (pH7.0) solution to concentration of 10% (w/v). AR-s standard solution is used with various concentration by diluting after preparing a solution of 1 mg/ml concentration by mixing 73 μl of 40 mM AR-S to 10% 927 μl of cetylpyrinidinium chloride solution.

TABLE 3

Effect inhibiting osteoclast cell formation depending on a kind of beta-glucan

| | Inhibiting percentage for osteoclast cell formation (%) | | | | |
| --- | --- | --- | --- | --- | --- |
| Conc. | SM2001 | yeast | pustulan | Youngi mushroom | Chima mushroom |
| $1 \times 10^{-6}$ | 60.5 ± 2.0 | 34.7 ± 5.0 | 27.6 ± 12.0 | 34.7 ± 21.6 | 21.3 ± 6.7 |
| $1 \times 10^{-7}$ | 35.1 ± 7.6 | 9.2 ± 0.9 | 6.1 ± 0.7 | 29.0 ± 3.4 | 31.2 ± 4.5 |

3) Activity Experiment of Osteoblast Cell

The prepared sample is added again to the plate described in the above item 1) every 3 days after removing all medium. After 15 days of cultivation, the medium is removed perfectly and washed with pure water several times. And 1 ml of 10% formalin solution is added to each well to fix for 30 minutes, and then washed with water 1 times, and then added Alizarin Red S (40 mM Alizarin Red S) dyeing liquid or Vorlcossa' (5% silver nitrate) dyeing liquid with 500 μl respectively, and reacted during 30 minutes, and washed with water several times, and then dried.

4) Analysis of Result

We can measure an accumulated amount of phosphorus or calcium by calculating area through dyeing or by absorbance of an extracted dyeing liquid in case of AR-S. A measurement of area is expressed with percentage (%) of a dyed area comparing with control group, wherein a dyed area can be measured with Image analyzer (Laica Co.). Also, in case of measurement of an accumulated amount of calcium by AR-S dyeing method, a calculation of area is carried out by the same method with the above, it is also possible to measure by absorbance through an extraction of AR-S among dyeing liquid. To extract AR-S from a dyed plate, 10% cetylpyrinidinium chloride solution is added with each 500 μl, and then reacted at 37° C. during 2 hours. An absorbance of the extracted AR-S solution is measured at 560 nm, an exact amount of the extracted AR-S is calculated with using a standard graph made out by measuring an absorbance according to a concentration of AR-S solution.

TABLE 4

Effect accelerating osteoblast cell formation of the water soluble beta-1,3/1,6-glucan derived from *Aureobasidium pullulans* SM2001

| Sample | $1 \times 10^{-5}$(g/ml) | | $1 \times 10^{-7}$(g/ml) | |
|---|---|---|---|---|
| | Amount of AR-S(μg/ml) | Osteoblast cell activity(%) | Amount of AR-S(μg/ml) | Osteoblast cell activity(%) |
| Beta-glucan | 335 ± 3 | 115 | 390 ± 38 | 183 |
| Control | 291 ± 25.6 | 100 | 213 ± 64.1 | 100 |

As shown the above table 4, the water soluble beta-1,3/1,6-glucan derived from *Aureobasidium pullulans* SM2001 show more excellent effect accelerating osteoblast cell formation than the control group. From this result, we can find out that the water soluble beta-1,3/1,6-glucan derived from *Aureobasidium pullulans* SM2001 is effective for a formation of bone through accumulation of calcium in osteoblast cell.

Example 6

Effect Accelerating Osteoblast Cell Formation Depending on a Kind of Beta-glucan As shown the above example 5, the beta-glucan derived from *Aureobasidium pullulans* SM2001 show an excellent effect accelerating osteoblast cell formation. Therefore, we try to research an effect accelerating osteoblast cell formation depending on a kind of beta-glucan. A sample of beta-glucan derived from yeast, pustulan, Youngi mushroom and Chima mushroom other than said beta-glucan derived from SM2001 strain are each prepared according to the same method of the above example 5. An effect of these samples on accelerating osteoblast cell formation is searched and its result is shown at table 5.

TABLE 5

Effect accelerating osteoblast cell formation depending on a kind of beta-glucan

| | Accelerating percentage for osteoblast cell formation (%) | | | | | |
|---|---|---|---|---|---|---|
| Conc. | control | SM2001 | yeast | pustulan | Youngi mushroom | Chima mushroom |
| $1 \times 10^{-5}$ | 291 ± 25 | 335 ± 35 | 160 ± 27 | 122 ± 18 | 151 ± 34 | 122 ± 6 |

As shown the above table 5, most beta-glucan do not show an effect accelerating osteoblast cell formation, but the water soluble beta-1,3/1,6-glucan of acidic form derived from *Aureobasidium pullulans* SM-2001 show an excellent effect accelerating osteoblast cell formation thuough an accumulation of calcium in osteoblast cell. Namely, the water soluble beta-1,3/1,6-glucan derived from *Aureobasidium pullulans* SM2001 has an excellent effect accelerating osteoblast cell formation as well as an effect suppressing differentiation of osteoclast cell and inhibiting formation of osteoclast cell, thereby can confirming a high possibility of application as a preventing agent and treating agent of osteoporosis.

Example 7

Effect on Anti-osteoporosis of Beta-glucan

To find out an effect on anti-osteoporosis of the beta-1,3/1,6-glucan derived from *Aureobasidium pullulans* SM2001 (hereinafter, referred as "beta-glucan"), we compare its effect with Fosamax, a treating agent of osteoporosis which is available at market, through in vivo experiment.

1) Treatment of Experimental Animal and Sample.

25 ddY female mice (age of 6 weeks, SLC, Japan) are used after adaptation during 7 days. The above animals are grouped each 5 and bred in a cage made of polycarbonate under the condition of temperature of 20~25° C. and humidity of 30~35%. A cycle of light and darkness is controlled to 12 hours: 12 hours. Feed stuff (Samyang Co., Korea) and water is fed freely. For 20 mice, the both ovary is taken out (ovary extraction : disclosing the both ovary, and then removing all of the both ovary, and then suturing with the same method), and for 5 mice, only sham surgical operation is carried out (sham surgical operation disclosing the both ovary by cutting (3 cm) a skin and an abdominal muscle, and then closing using a skin suturing technique). For the purpose of therapeutic research, a treatment is started after 4 weeks of the ovary extraction, each sample is administrated during 4 weeks.

All sample is stored at a refrigerate (−10° C.) to prevent from a moisture and light. While corn oil is used as a carrier for sample, it is administrated with a dose of 10 ml/kg using an oral administration catheter. A group of beta-glucan is divided to two groups. to one group is administrated with a dose of 25 mg/10 ml/Kg (GLU(A)) in the abdominal cavity by injector, to the other group is administrated with a dose of 100 mg/10 ml/Kg (GLU(B)) through oral. Fosamax (sodium alendronate) is dissolved in distilled water as a carrier with a concentration of 10 mg/10 ml/Kg and then administrated. A dose and administrating schedule of each sample is shown at table 6.

TABLE 6

Treating method of each experimental group

| | Treatment | Dose | Name | Carrier | Route | Schedule |
|---|---|---|---|---|---|---|
| Sham surgical operation | Sham surgical operation | 10 ml/kg | Sham | Distilled water | Oral | For 4 weeks, 1 times per 1 day. |
| Ovary extraction | Control | 10 ml/kg | Control | Distilled water | Oral | |
| | Fosamax | 10 mg/kg/ 10 ml | FOSA | Distilled water | Oral | |
| | Beta-glucan | 25 mg/kg/ 10 ml | GLU(A) | Corn oil | Abdominal cavity | |
| | Beta-glucan | 100 mg/kg/ 10 ml | GLU(B) | Corn oil | Abdominal cavity | |

For histological analysis of experimental animals, the left thigh of each mouse is separated to fix in 10% neutral buffer formalin (NBF) solution, and then delimed during 5 days at delime solution [24.4% formic acid, 0.5N NaOH] (the mixed delime solution is exchanged each day one times during 3 days). And then it is fixed to paraffin and then made fraction (3~4 cm) and dyed with hematoxylineosin.

Body weight, weight of both thigh, histological change including trabecular bone volume (TBV) % and Cortical bone thickness (Cbt) is analyzed. Also, histomorphometric changes of the trochoid bone of left thigh are observed. All experimental result of followings are shown with means±standard deviation. A statistical analysis is carried out by using SPSS For Windows (Release 6.1.3., SPSS Inc, USA) and Mann-Whitney U-Wilcoxon Rank Sum W test(M-W test).

2) Body Weight

Change of body weight and increasing part is calculated after immediately surgical operation, after 4 weeks of surgical operation, after administration, and each week one times during experiment period. Experimental animals do not feed during overnight to reduce an error due to feeding before administration and sacrifice (except feeding water, about 18 hours). Also, an increasing part of body weight during adapting period (Increasing part I) and administrating period (Increasing part II) is calculated as followings.

Increasing part I=(body weight after 4 weeks of surgical operation−body weight after surgical operation)

Increasing part II=(body weight after sacrifice−body weight after administration)

Body weight and an increasing part after ovary extraction and administration are shown at table 7. There is not any significant observation for change of body weight due to ovary extraction except some deviation due to a differentiation of obesity between an individual. This is a general phenomenon existing at rodents. [Lorden J. F. and Caudle A., *Neurobehav. Toxicol. Teratol.,* 8, 509~519 (1986)]. However, in all groups of ovary extraction, some increase of body weight is observed, it is thought as a general phenomenon being happened at the state of lack of estrogen.

TABLE 7

Change of body weight of each experimental group

| | A | B | C | D | E |
|---|---|---|---|---|---|
| Sham | 24.80 ± 1.47 | 30.90 ± 3.72 | 30.32 ± 1.99 | 33.34 ± 2.07 | 33.86 ± 2.19 |
| Control | 25.08 ± 0.85 | 36.62 ± 3.33** | 34.42 ± 2.88** | 36.80 ± 3.70 | 36.88 ± 3.97 |
| FOSA | 25.30 ± 1.17 | 33.68 ± 2.61 | 31.56 ± 1.81 | 34.46 ± 2.76 | 32.86 ± 4.20 |
| GLU(A) | 25.36 ± 0.66 | 35.04 ± 2.14** | 32.78 ± 2.01 | 37.00 ± 1.81** | 38.38 ± 4.53 |
| GLU(B) | 25.08 ± 1.12 | 34.80 ± 1.15** | 32.84 ± 0.71** | 35.08 ± 1.37 | 35.30 ± 1.52 |

| | F | G | H | I |
|---|---|---|---|---|
| Sham | 34.36 ± 2.19 | 32.04 ± 1.75 | 6.10 ± 5.00 | 1.72 ± 1.30 |
| Control | 37.44 ± 4.71 | 35.66 ± 4.69 | 11.54 ± 3.36** | 1.24 ± 2.34 |
| FOSA | 37.02 ± 3.93 | 31.70 ± 3.73 | 8.38 ± 2.10 | 3.26 ± 2.73 |

TABLE 7-continued

| | Change of body weight of each experimental group | | | |
|---|---|---|---|---|
| GLU(A) | 44.36 ± 2.06*, # | 41.42 ± 1.98* | 9.68 ± 1.06 | 8.64 ± 1.71*, # |
| GLU(B) | 36.54 ± 1.37** | 34.72 ± 1.20** | 9.72 ± 1.06 | 1.88 ± 1.25 |

Remark)
A: after immediately surgical operation, B: after 4 weeks of surgical operation, C: after immediately administration, D: after 1 week of administration, E: after 2 weeks of administration, F: after 4 weeks of administration, G: after sacrifice, H: Increasing part I, I: Increasing part II. ;

Particularly, it is considered that a considerable increase at an increasing part of body weight during administrating period and after 4 weeks of administration in group GLU(A) is due to existing of sample not being absorbed in abdominal cavity. Actually, in group GLU(A), much amount of sample not being absorbed is observed in abdominal cavity. From this result, we can determine that corn oil is not suitable for a carrier for inserting beta-glucan, it is necessary to select the other carrier other than corn oil by another research in vivo such as research of long term (about 3 weeks) using rat of ovary extraction.

3) Weight of Bone

After sacrifice, a weight of bone of both thighs is calculated with g unit. To reduce an error arising from a difference of individual body weight, a weight of bone is calculated with relative weight as following equation.

Weight of bone=[(absolute weight of bone/body weight at sacrifice)×100]

A change for an absolute weight of bone and a relative weight of bone after ovary extraction and administration are summarized at table 8. A significant reduction is observed for relative weight of bone in control group than sham group. However, there is not any significant observation for change in experimental group than control group. But a significant reduction is observed for relative weight of bone in GLU(A) group than control group (p<0.01). There must be deviation on a weight of bone according to a condition of bone and research. Therefore, it is received that a change of bone weight excepting an ash bone weight is not a definite index [Yamamoto M., et al., *Endocrinology*, 139, 1411~1419 (1998)]. Particularly, in the case of this experiment, a wet weight is only measured. Further, we can infer that a considerable change of relative weight of bone observes in GLU(A) group is not due to any toxin or effect of sample, but is to an accumulation of sample not being absorbed in abdominal cavity as the above description. It is difficult to regard a change of bone weight with a definite index since a change of bone weight is not a measurement of ash bone weight but only a measurement of wet weight.

TABLE 8

Weight of bone of each experimental group

| Weight of bone | Absolute weight of bone | Relative weight of bone |
|---|---|---|
| Sham | 0.085 ± 0.008 | 0.265 ± 0.020 |
| Control | 0.081 ± 0.007 | 0.227 ± 0.014* |
| FOSA | 0.075 ± 0.006* | 0.217 ± 0.015* |
| GLU(A) | 0.078 ± 0.006 | 0.189 ± 0.015*, # |
| GLU(B) | 0.082 ± 0.006 | 0.236 ± 0.019** |

Remark)
When comparing with control *p < 0.01, **p < 0.05, #p < 0.01

4) Measurement of Trabecular Bone Volume (TBV)

TBV is calculated by using a Auto Image analysis (analySIS Image Processing; SIS, Germany) under 100 magnifications on a microscope (Zeiss, Germany) for regular size of trabecular bone at the trochoid bone of right thigh (excluding a growth plate). TBV is calculated with (%) unit.

TBV after ovary extraction and administration is summarized at table 9. A significant reduction (p<0.01) is observed for TBV in all experimental groups than control group after ovary extraction. However, a significant increase (p<0.01) is observed for TBV of Fosamax and beta-glucan groups than control group. Furthermore, the order of increasing rate of TBV regarding to control group is Fosamax>>GLU(A)≧GLU(B). Therefore, it can be determined that beta-glucan has a positive effect to inhibit a reduction of TBV induced from ovary extraction.

5) Measurement of a Histological Index of Trabecular Bone

A trabecular bone thickness (Tbt), a number of trabecular bone (Tbn), and a trabecular bone length (Tbl) are calculated by using a Auto Image analysis (analySIS Image Processing; SIS, Germany) under 100 magnifications on a microscope (Zeiss, Germany) for regular size at the trochoid bone of left thigh (excluding a growth plate). Tbt and Tbl are calculated with μm unit, and Tbn is calculated with a number of trabecular bone/all section of the trochoid bone section. Tbt and Tbl is calculated at trabecular bone that is most developed in a regular size of the trochoid bone section.

A change of Tbt after ovary extraction and administration is summarized at table 9. A significant reduction (p<0.01) is observed for Tbt in control group than sham group after ovary extraction. However, a significant increase (p<0.01 and p<0.05) is observed for Tht of all beta-glucan groups, GLU (A) and GLU(B) than control group. Furthermore, the order of increasing rate of Tbt regarding to control group is Fosamax>GLU(A)≧GLU(B). Therefore, it can be determined that beta-glucan has a considerable effect to inhibit a reduction of Tbt induced from ovary extraction. But its effect is similar to Fosamax or is less than it.

A change of Tbn after ovary extraction and administration is summarized at table 9. A significant reduction (p<0.01) is observed for Tbn in control group than sham group after ovary extraction. However, a significant increase (p<0.01 and p<0.05) is observed for Tbn of all beta-glucan and Fosamax groups than control group. Furthermore, the order of increasing rate of Tbn regarding to control group is Fosamax>>GLU (B)≧GLU(A). Therefore, it can be determined that beta-glucan has a considerable effect to inhibit a reduction of Tbn induced from ovary extraction, and its effect is less than Fosamax.

A change of Tbl after ovary extraction and administration is summarized at tabe 9. A significant reduction (p<0.01) is observed for Tbl in control group than sham group after ovary extraction. However, a significant increase (p<0.01 and p<0.05) is observed for Tbl of all experimental groups than control group. Furthermore, the order of increasing rate of Tbl regarding to control group is GLU(A)>GLU(B)>>Fosamax. Therefore, it can be determined that beta-glucar has a considerable effect to inhibit a reduction of Tbl induced from ovary extraction, and its effect is higher than Fosamax.

6) Cortical Bone Thickness (Cbt)

Cbt is measured at the trochlea neck of thigh and calculated by using a Auto Image analysis (analySIS Image Processing; SIS, Genmany) under 200 magnifications on a microscope (Zeiss, Germany) at prepared histological sample.

A change of Cbt after ovary extraction and administration is summarized at table 9. A significant reduction (p<0.01) is observed for Cbt in all groups than sham group after ovary extraction. However, a significant increase (p<0.01 and p<0.05) is observed for Cbt of beta-glucan groups than control group. Fosamax group shows a similar value to control group. Therefore, it can be determined that beta-glucan has a considerable effect to inhibit a reduction of Cbt induced from ovary extraction, and its effect is higher than Fosamax.

group are lower than sham group, but notable increase compared with control group is observed (FIGS. 4(2d) and (2e)).

When summarizing the above description, beta-glucan has some positive effect in inhibiting a histomorphometric changes of trabecular bone of trochlea neck's cortical bone and trochlea epiphyseal region of left thigh induced by ovary extraction.

In conclusion, it can be considered that beta-glucan is effective in anti-osteoporosis inhibiting a change of a cortical bone and a trabecular bone induced by ovary extraction. An efficacy of beta-glucan for a trabecular bone is some lower than Fosamax, but an efficacy of beta-glucan for a cortical bone is some higher, on the contrary. A histomorphometric index for the ilium has been generally used as criteria that verify an efficacy of anti-osteoporosis, and deemed as most predictable method [Murakami et al., *J. Bone Miner. Res.,* 9, 1355~1364 (1994); Weinreb et al., *Virchows Arch.* 431, 449~452 (1997)].

The invention claimed is:

1. A method for treating osteoporosis by administering a pharmaceutical composition comprising a therapeutically

TABLE 9

Histological change of thigh such as trabecular bone, Cortical bone in each experimental group.

| Group (n = 5) | Sham | Control | FOSA | GLU(A) | GLU(B) |
|---|---|---|---|---|---|
| TBV (%) | 47.31 ± 5.95 | 20.23 ± 1.72* | 35.13 ± 4.28 | 27.26 ± 3.95*,# | 26.26 ± 3.42*,# |
| Tbt(μm) | 111.00 ± 14.87 | 66.40 ± 11.70* | 93.60 ± 9.56## | 90.60 ± 7.92**,## | 90.00 ± 9.19**,## |
| Tbn | 15.00 ± 2.92 | 3.40 ± 1.14* | 15.20 ± 2.77# | 7.00 ± 1.41*,## | 9.20 ± 1.30**,# |
| Tbl(μm) | 1476.00 ± 233.08 | 524.40 ± 176.78* | 759.40 ± 89.17*,## | 1111.00 ± 91.44*,# | 985.40 ± 104.08*,# |
| Cbt(μm) | 271.40 ± 36.98 | 99.20 ± 20.46* | 102.50 ± 22.29* | 151.72 ± 22.92*,# | 139.60 ± 12.22*,## |

Remark)

*p < 0.001, **p < 0.05(comparing with sham group), #p < 0.01, ##p < 0.05(comparing with control group)

8) Analysis of Histomorphometric Changes

A histomorphometric change of left thigh is analyzed by dyeing with Hematoxylin-Eosin.

The histomorphometric changes of left thigh are shown at FIG. 3. In FIG. 3(1a), it can be represented a trabecular bone of sham group which well developed relatively from a growth plate to a cavity of bone marrow. However, as shown FIG. 3(1b), there is hardly observed an extended trabecular bone in the case of control group. There is observed many an extended trabecular bone in the case of Fosamax and beta-glucan group than control group. However, its width or number is lower than sham group (FIG. 3(1c)~(1e)).

The histomorphometric changes of a cortical bone of left thigh are shown at FIG. 4. A well-developed osteo-membrane and hard bones are also shown in sham group (FIG. 4(2a)). However, there is observed a reduction of entire width for a cortical bone in the case of control group. Also, a large pore that cells such as bone marrow cell have is observed in this group (FIG. 4(2b)). Some increased or similar width and histomorphometric property comparing with control group are observed at Fosamax group (FIG. 4(2c)). However, a width and density of cortical bone at GLU(A) and GLU(B)

effective amount of beta-1,3/1,6 glucan, characterized in that said beta-1,3/1,6 glucan is produced from *Aureobasiduim pullulans* SM2001 (SCCM 10307) and represented by the following formula 1 having a lactate as a substituent:

Formula 1:

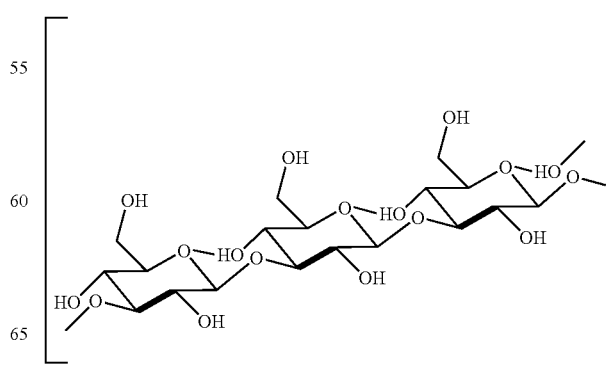

-continued
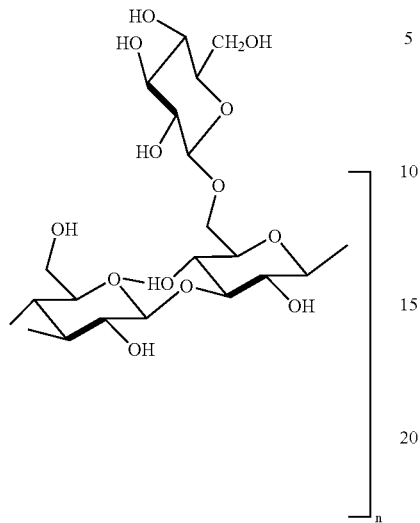
* * * * *